US007014660B2

(12) United States Patent
Fenning et al.

(10) Patent No.: US 7,014,660 B2
(45) Date of Patent: Mar. 21, 2006

(54) PROSTHETIC KNEE WITH REMOVABLE STOP PIN FOR LIMITING ANTERIOR SLIDING MOVEMENT OF BEARING

(75) Inventors: John B. Fenning, Fort Meyers, FL (US); Michael J. Pappas, Jensen Beach, FL (US)

(73) Assignee: Biomedical Engineering Trust I, South Orange, NJ (US)

( * ) Notice: Subject to any disclaimer, the term of this patent is extended or adjusted under 35 U.S.C. 154(b) by 329 days.

(21) Appl. No.: 10/410,779

(22) Filed: Apr. 9, 2003

(65) Prior Publication Data

US 2003/0195634 A1  Oct. 16, 2003

Related U.S. Application Data

(60) Provisional application No. 60/371,607, filed on Apr. 10, 2002.

(51) Int. Cl.
*A61F 2/38* (2006.01)

(52) U.S. Cl. .................................... 623/20.29

(58) Field of Classification Search .. 623/20.14–20.15, 623/20.21–20.25, 20.27–20.32, 20.34
See application file for complete search history.

(56) References Cited

U.S. PATENT DOCUMENTS

| 4,001,896 | A | * | 1/1977  | Arkangel .................. 623/20.24 |
| 4,007,495 | A |   | 2/1977  | Frazier |
| 4,219,893 | A |   | 9/1980  | Noiles |
| 4,224,697 | A | * | 9/1980  | Murray et al. ........... 623/20.25 |
| 4,309,778 | A |   | 1/1982  | Buechel et al. |
| 4,340,978 | A |   | 7/1982  | Buechel et al. |
| 4,353,136 | A |   | 10/1982 | Polyzoides et al. |
| 4,470,158 | A |   | 9/1984  | Pappas et al. |
| 4,673,408 | A | * | 6/1987  | Grobbelaar .............. 623/20.29 |
| 4,728,332 | A |   | 3/1988  | Albrektsson |
| 4,834,081 | A | * | 5/1989  | Van Zile ...................... 606/99 |
| 4,950,297 | A |   | 8/1990  | Elloy et al. |
| 5,007,933 | A | * | 4/1991  | Sidebotham et al. ..... 623/20.27 |
| 5,194,066 | A | * | 3/1993  | Van Zile .................. 623/20.15 |
| 5,370,701 | A |   | 12/1994 | Finn |
| 5,395,401 | A | * | 3/1995  | Bahler ..................... 623/20.29 |
| 5,702,466 | A | * | 12/1997 | Pappas et al. ........... 623/20.29 |
| 6,080,195 | A | * | 6/2000  | Colleran et al. ......... 623/20.32 |
| 6,210,443 | B1| * | 4/2001  | Marceaux et al. ....... 623/20.33 |
| 6,217,618 | B1| * | 4/2001  | Hileman .................. 623/20.33 |
| 6,238,434 | B1|   | 5/2001  | Pappas |
| 6,319,283 | B1| * | 11/2001 | Insall et al. ............. 623/20.33 |
| 6,458,160 | B1| * | 10/2002 | Biegun et al. ........... 623/20.27 |
| 6,475,241 | B1| * | 11/2002 | Pappas .................... 623/20.29 |
| 6,491,726 | B1|   | 12/2002 | Pappas |

(Continued)

FOREIGN PATENT DOCUMENTS

DE     25 45 821     4/1976

(Continued)

*Primary Examiner*—Eduardo C. Robert
*Assistant Examiner*—Annette Reimers
(74) *Attorney, Agent, or Firm*—Anthony J. Casella; Gerald E. Hespos

(57) ABSTRACT

A knee prosthesis includes a femoral component, a tibial component, a bearing and a control arm. The bearing is in articular bearing engagement with the femoral component and in sliding and rotational bearing engagement with the tibial component. Movement of the bearing relative to the tibial component is controlled by a control arm. The anterior extreme of the control arm includes a removable stop for limiting anterior movement of the bearing relative to the tibial component.

11 Claims, 5 Drawing Sheets

U.S. PATENT DOCUMENTS

| | | | |
|---|---|---|---|
| 6,755,864 B1 * | 6/2004 | Brack et al. | 623/20.29 |
| 6,764,516 B1 * | 7/2004 | Pappas | 623/20.29 |
| 6,797,005 B1 * | 9/2004 | Pappas | 623/20.27 |
| 2001/0034555 A1 * | 10/2001 | Pappas | 623/20.29 |
| 2002/0156535 A1 * | 10/2002 | Pappas | 623/20.29 |
| 2003/0009229 A1 * | 1/2003 | Pappas | 623/20.27 |

FOREIGN PATENT DOCUMENTS

| | | |
|---|---|---|
| DE | 25 50 704 | 5/1976 |
| DE | 35 29 894 | 3/1987 |
| DE | 91 10 504.8 | 12/1991 |
| EP | 0 186 471 | 7/1986 |
| EP | 0 349 173 | 1/1990 |
| EP | 0 519 873 | 12/1992 |
| EP | 0 529 408 | 3/1993 |
| FR | 2 663 536 | 12/1991 |
| GB | 2 223 950 | 4/1990 |
| WO | WO 92/08424 | 5/1992 |

* cited by examiner

PROSTHETIC KNEE WITH REMOVABLE STOP PIN FOR LIMITING ANTERIOR SLIDING MOVEMENT OF BEARING

This application claims priority on U.S. Provisional Patent Appl. No. 60/371,607, filed Apr. 10, 2002, the contents of which are hereby incorporated by reference.

BACKGROUND OF THE INVENTION

1. Field of the Invention

A prosthetic knee joint is provided with a femoral component, a tibial component and a bearing between the femoral and tibial components. The bearing is capable of rotational movement on the tibial component and anterior-posterior sliding movement on the tibial component in response to flexion of the knee.

2. Description of the Related Art

U.S. Pat. No. 5,702,466 shows a knee prosthesis with a tibial component that has a superior bearing surface. The prosthesis further includes a femoral component with an inferior articular bearing surface. A bearing is disposed between the tibial and femoral component and includes an inferior surface in rotating and sliding bearing engagement with the superior surface of the tibial component. The bearing further includes a superior surface in articular bearing contact with the inferior surface of the femoral component. Movement of the bearing on the tibial component is controlled by a control arm. More particularly, the bearing includes a groove that extends in an anterior-posterior direction in the inferior surface of the bearing. A control arm assembly is pivotally mounted to the tibial component and includes an arm that is slidably engaged in the groove of the bearing. Thus, the bearing and the control arm can rotate together on the superior surface of the tibial component. Additionally, the bearing can slide on the superior surface of the bearing and along the arm of the control arm assembly.

The ability of the tibia to move forward relative to the femur is critical in the achievement of maximum passive flexion. If the tibia does not so move its posterior aspect will impinge sooner against the posterior aspect of the femur, thereby limiting flexion sooner. Where the posterior cruciate is not salvageable, or viable, the posterior stabilized knee device shown in U.S. Pat. No. 6,491,726 produces such rearward motion. Where a viable posterior ligament is present one can use this ligament to generate this posterior motion of the femur on the tibia (rollback).

A knee device that allows anterior-posterior motion of the femur on the tibia can allow maximum passive flexion even in the absence of a competent posterior cruciate ligament. As the leg is forced into maximum passive flexion the proximal tibia will be forced forward by pivoting on the impinging proximal, posterior tibial soft tissue if the prosthetic knee allows anterior motion of the proximal tibia. The absence of a competent posterior ligament, coupled with a device that permits anterior-posterior motion of the femur on the tibia, unfortunately, results in anterior-posterior instability of the knee. If this motion is unconstrained, except by the action of functioning ligaments, then the instability is likewise unconstrained and is undesirable.

The position of the tibia during maximum passive flexion activities typically requires substantial axial rotation of the tibia relative to the femur. This rotation (approximately 25°) may be sufficient to produce placement of one of the posterior femoral condyles to be anterior to the posterior edge of its corresponding tibial condyle. That is, the femoral condyle may overhang the tibia on one side. Thus a knee replacement should also allow such rotation, but preferably without overhang. A device where the bearing can rotate on the tibial component is ideal for such a situation.

The prosthesis shown in U.S. Pat. No. 5,702,466 can be used for a knee device to exploit the ability of the posterior cruciate ligament to produce rollback and to provide anterior-posterior translation and axial rotation needed to obtain maximum passive flexion. Unfortunately there have been some problems experienced with this design in clinical use. Anterior knee pain, particularly on flexion, is one of these problems. This probably results from an incompetent posterior cruciate ligament producing anterior motion of the femur on the tibia rather than rollback. This anterior motion will produce impingement between the anterior aspect of the bearing and soft tissue structures of the knee. Such impingement can produce such pain. This incompetence is quite common and is the reason that anterior motion of the femur relative to the tibia is commonly observed with knee designs that allow such motion.

A posterior stabilized knee, as shown in U.S. Pat. No. 6,475,241 or U.S. Pat. No. 6,491,726 is preferred for those situations where a competent posterior ligament is not present. More particularly, the designs shown in U.S. Pat. No. 6,475,241 and U.S. Pat. No. 6,491,726 reliably produce needed rollback and provided needed axial bearing rotation. Further, these designs limit anterior-posterior instability to essentially normal limits. Where there is a competent posterior cruciate ligament a prosthetic device of the type shown in U.S. Pat. No. 5,702,466 seems preferable since it allows the natural structures to provide such action rather than the mechanical structures of the posterior stabilized device.

The problem however is that the identification of a viable cruciate ligament is not easily accomplished by many surgeons and a once competent ligament may become incompetent. Thus it is desirable to improve the performance of the prosthesis shown in U.S. Pat. No. 5,702,466 in the presence of an incompetent posterior cruciate ligament.

FIGS. 11–13 of U.S. Pat. No. 5,702,466 show an embodiment where the arm of the control arm assembly is formed with a channel and where the bearing includes a shoulder engaged in the channel. The channel and the shoulder function to limit anterior movement of the bearing relative to the control arm and the tibial component and, hence, enhance stability in those situations where there is not a viable cruciate ligament or where the ligament becomes incompetent after implantation of the prosthesis. However, the interengageable channel and shoulder complicate implantation of the prosthesis and complicate removal of the prosthesis that may be required intraoperatively or during revision surgery.

Surgery to implant the prosthetic device shown in FIGS. 11–13 of U.S. Pat. No. 5,702,466 typically is completed by resecting the superior end of the tibia and the inferior end of the femur. The resected ends of the tibia and femur may be prepared further by forming cavities. The stem of the tibial component then is inserted into the cavity formed in the resected superior end of the tibia so that the platform of the tibial component is supported on the resected end of the tibia. The bearing then is assembled with the control arm and the cone that projects from the control arm is inserted into the conical recess in the tibial component. The femoral component then is mounted to the resected inferior surface of the femur. This sequence is required because the subassembly of the control arm and the bearing cannot be mounted easily into the conical recess of the tibial component once the femoral component has been mounted to the femur.

Revision surgery occasionally is necessary. One possible reason for revision surgery would be to replace a defective bearing. In this situation, the femoral component is likely to be properly implanted and perfectly functional. The presence of the properly implanted femoral component significantly complicates the revision surgery, particularly during the implantation of the new bearing and control arm assembly. This implantation is particularly impeded for those prostheses where the control arm assembly is formed with a channel and where the bearing includes a shoulder to engage the channel as depicted in FIGS. 11–13 of U.S. Pat. No. 5,702,466. Surgeons may try to retract the joint sufficiently so that the cone of the bearing/control arm subassembly can be inserted into the recess of the tibial component. However, such excessive retraction of the joint can stretch ligaments and complicate post-surgery recovery. In other instances, the surgeon may remove a properly implanted and perfectly functional femoral component so that the components of the prosthesis can be implanted during revision surgery in the same sequence employed during the initial surgery to implant the prosthesis. The femoral component often is secured in place by adhesive, bone tissue or some combination thereof. Hence, the removal of the properly implanted femoral component can damage the femur and contribute to post-surgery trauma for the patient.

The presence of the properly implanted femoral component also can complicate the removal of the bearing and control arm assembly during revision surgery for those instances where the arm of the control arm assembly is formed with a channel and where the bearing includes a shoulder engaged in the channel. In particular, the control arm must be removed with the bearing. However, the cone of the control arm is trapped in the recess of the tibial component. Problems of removing the bearing during revision surgery are less severe than problems relating to the implantation of a new bearing during revision surgery. In particular, the previously implanted bearing can be broken by the surgeon and removed in pieces. This solution is not ideal, but may be acceptable during the bearing-removal phase of revision surgery. However, this option is not available to implant a new bearing because the preferred new bearing is of unitary construction.

The subject invention was developed in view of these problems encountered during revision surgery. An object of the invention is to facilitate proper positioning of a bearing/control arm subassembly during revision surgery and particularly for those prosthetic joints that have structure for limiting anterior movement of the bearing relative to the control arm.

SUMMARY OF THE INVENTION

The invention relates to a knee prosthesis that has a femoral component having a superior surface for mounting to the resected inferior or distal end of a femur. The femoral component also has an inferior articular bearing surface with medial and lateral convex condyles. The knee joint prosthesis also includes a tibial component with an inferior face configured for mounting to the superior or proximal end of a resected tibia. The tibial component also has a superior bearing face. A bearing is disposed between the femoral and tibial components. The bearing includes an inferior bearing surface disposed in rotational and sliding bearing relationship with the superior surface of the tibial component. The bearing further includes a superior surface with concave condyles disposed in articular bearing engagement with the condyles of the femoral component. The concave superior surface of the bearing may be configured to provide surface contact with the condyles of the femoral component at full extension of the knee. However, the concave superior surface of the bearing is incongruent with the condyles of the femoral component during flexion, and achieves only line contact. The incongruency contributes to the generation of roll back during flexion, and hence contributes to anterior-posterior sliding movement of the bearing relative to the tibial component during flexion.

The knee joint prosthesis further includes a control arm assembly. The control arm assembly is rotatably engaged with the femoral component and is slidably engaged with the inferior surface of the bearing. More particularly, the inferior surface of the bearing may include anterior-posterior groove that slidably engages the control arm. Anterior portions of the control arm are formed with a stop pin that engage in a recess in the inferior surface of the bearing for limiting the amount of anterior sliding movement of the bearing on the tibial component and the control arm assembly. The engagement of the bearing with the stop pin on the control arm reduces or avoids possible impingement of the prosthesis with anterior knee tissues, thereby reducing anterior knee pain. The stop pin preferably is removably mounted to the control arm. More particularly, the stop pin preferably comprises attachment means for removable attachment of the stop pin to anterior portions of the control arm. The attachment means preferably is accessible from anterior portions of the assembled prosthesis.

DETAILED DESCRIPTION OF THE PREFERRED EMBODIMENTS

Figure 1:
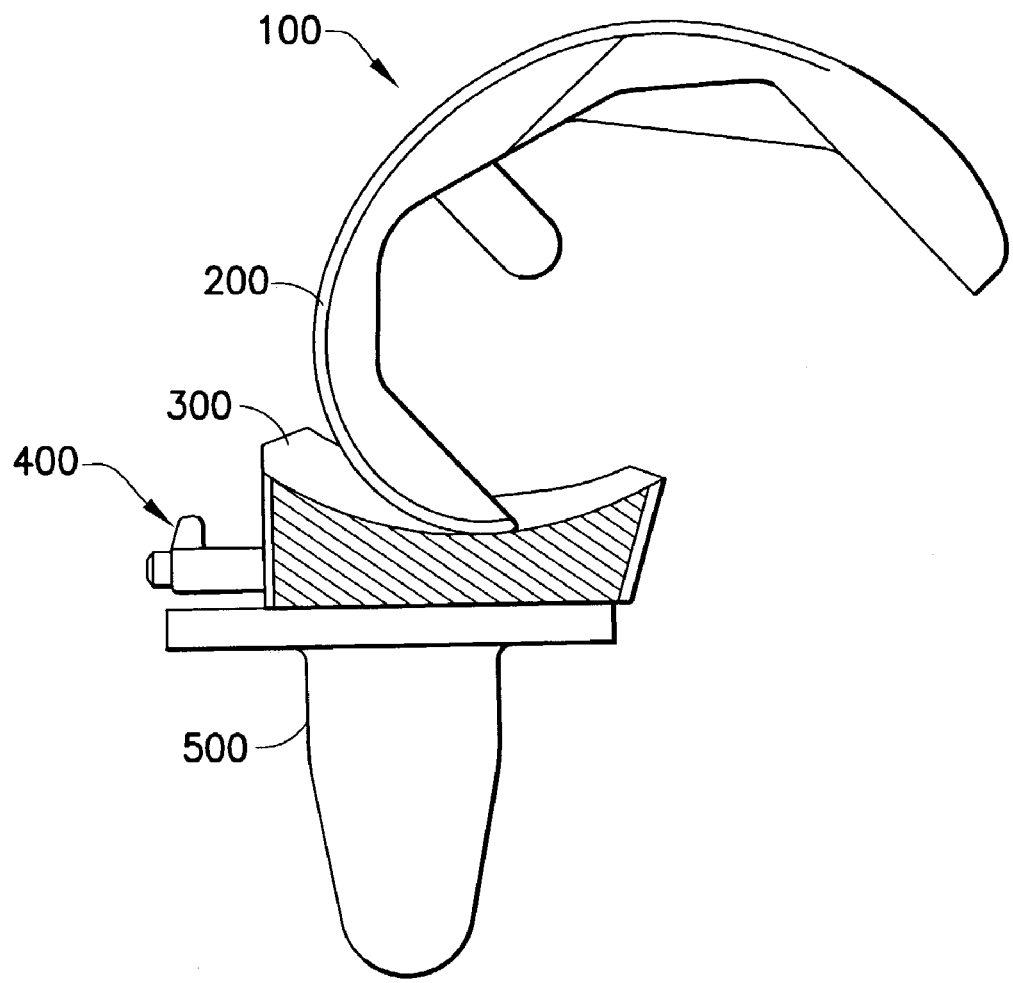
FIG. 1 is a side elevational view, partly in section, showing a knee joint prosthesis in accordance with the subject invention.

A prosthetic knee device in accordance with the invention is identified by the numeral 100 and is shown in FIG. 1, at 162° of flexion. This is the maximum human passive flexion even in Asian cultures where deep squatting and sitting on the floor is common. During such flexion the tibia, and thus the tibial component 500, move forward relative to the femur and the bearing 300 moves backward on the tibial component as shown. Such motion is necessary to achieve flexion of this magnitude.

The prosthetic knee device 100 comprises a femoral component 200, bearing 300, control arm 400 and a tibial component 500. The femoral and tibial components 200 and 500 respectively are identical to the femoral and tibial components in prior art LCS prosthetic knees.

Figure 2:
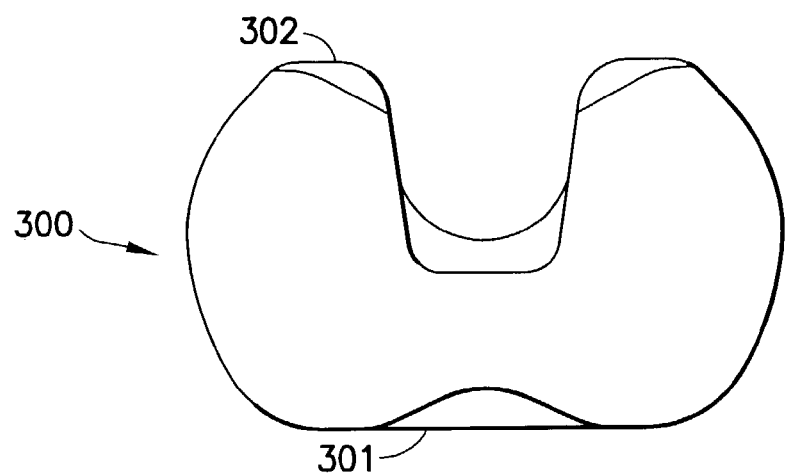
FIG. 2 is a top plan view of the bearing shown in FIG. 1.
Figure 3:
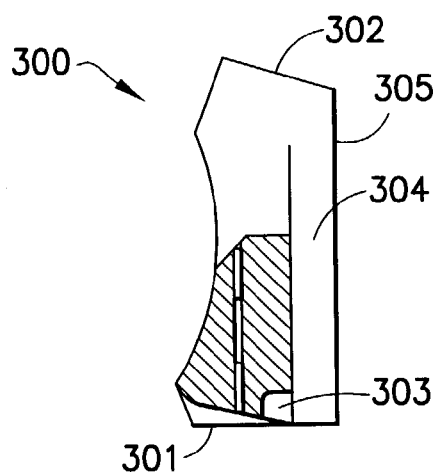
FIG. 3 is a side elevational view, partly in section, of the bearing.
Figure 4:
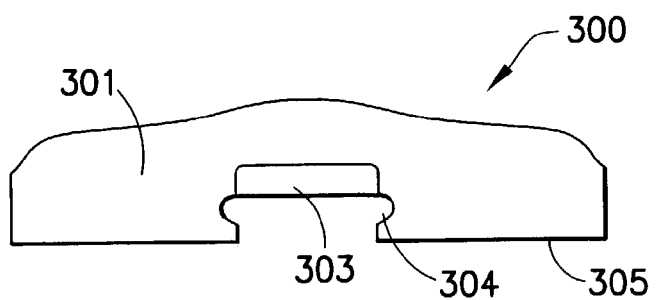
FIG. 4 is a front elevational view of the bearing.

The bearing 300 is shown in FIGS 2–4. More particularly, the bearing 300 is formed from an ultra high molecular weight polyethylene and is similar to the earlier Flexglide bearing except the distance from its anterior surface 301 to its posterior surface 302 is somewhat less than the earlier design so as to reduce the potential for tissue impingement on deep flexion. The added width of the earlier bearing was an overreaction to the problem of spinout of the original rotating platform bearing. The original Flexglide bearing has the same plan form as the rotating platform bearing modified to improve resistance to spinout. Spinout is, however, not a problem with the Flexglide bearing and this increased width is not necessary. The bearing 300 also contains a stop recess 303 at an anterior and inferior extreme position on the bearing and a dovetail groove 304 that extends along the inferior surface 305 of the bearing from the anterior extreme to the posterior extreme. Anterior portions of the dovetail groove 304 align with the recess 303.

Figure 5:
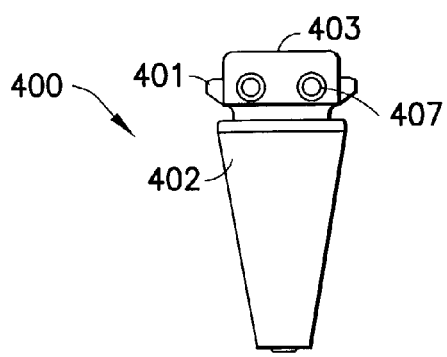
FIG. 5 is a front elevational view of the control arm assembly.
Figure 6B:
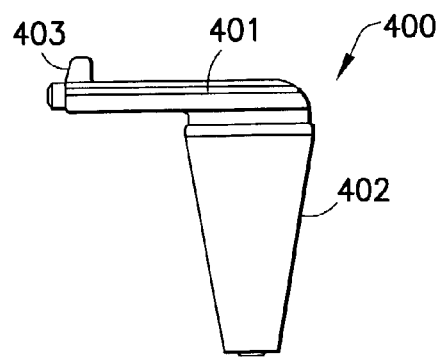
FIG. 6B is a side elevational view of the control arm assembly in its assembled condition.
Figure 6A:
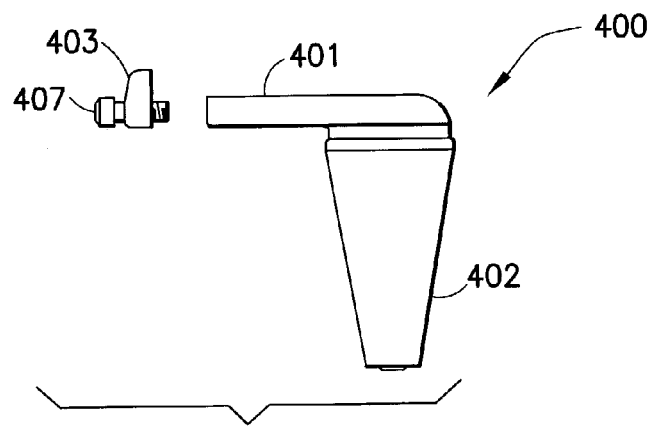
FIG. 6A is an exploded side elevational view of the control arm assembly.
Figure 7A:
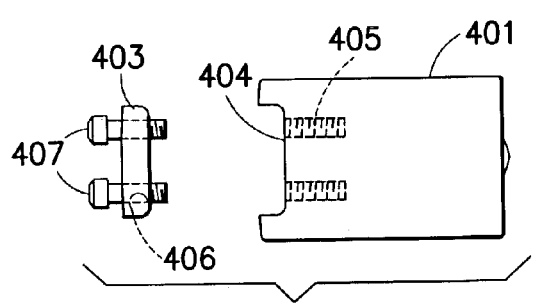
FIG. 7A is an exploded top plan view of the control arm assembly.
Figure 7B:
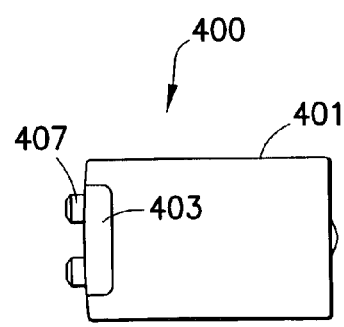
FIG. 7B is a top plan view of the control arm assembly in its assembled condition.
Figure 8:
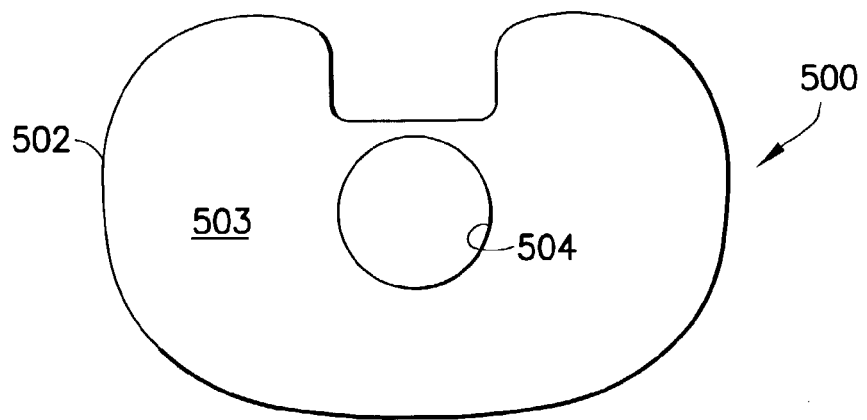
FIG. 8 is a top plan view of the tibial component.
Figure 9:
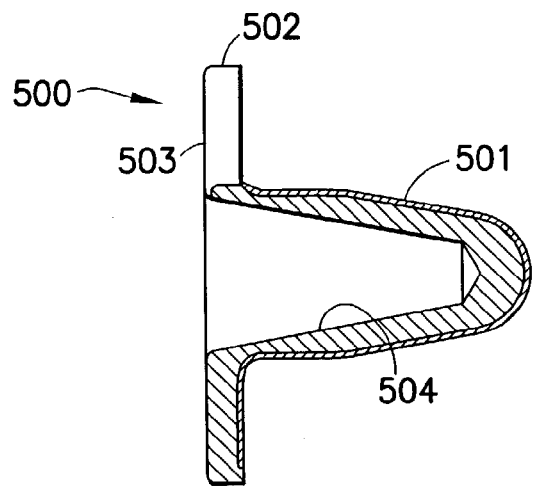
FIG. 9 is a cross-sectional view of the tibial component taken along an anterior-posterior plane.
Figure 10:
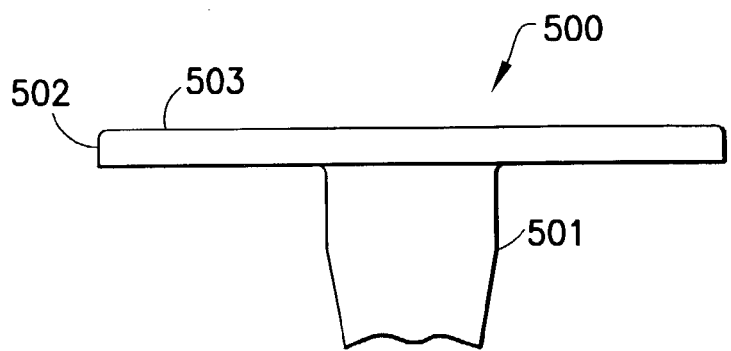
FIG. 10 is a front elevational view of the tibial component.

The control arm assembly 400 shown in FIGS. 5–7 is similar to that of U.S. Pat. No. 5,702,466 except that the dovetail-shaped arm 401 is wider to provide additional stability of the control arm assembly 400. This stability is desirable since the cone 402 of this design is smaller than that of the original for the larger size knees. The control arm assembly 400 also contains a removable anterior stop 403 removably mounted to anterior portions of the control arm 401. More particularly, the control arm 401 is formed with an anterior notch 404 and two threaded apertures 405 extending posteriorly into the anterior notch 404. The stop 403 is configured to fit closely in the notch 404. Both the control arm 401 and the stop 403 are formed from a metallic material. An exemplary stop 403 according to the present disclosure is formed with two apertures 406 extending therethrough and disposed to align with the threaded apertures 405 in the notch 404 when the stop 403 is mounted in the notch 404. The exemplary stop 403 further includes two screws 407 rotatably trapped in the apertures 406 of the stop 403. The screws 407 are dimensioned for threaded engagement in the threaded apertures 405 of the control arm 401. Thus, the screws 407 can be used to removably mount the stop 403 to the anterior end of the control arm 400, and function as attachment means according to the present disclosure. Alternative attachment means which function to removably secure the stop are contemplated. As shown in FIG. 6B, the stop 403 is dimensioned to extend superiorly from anterior portions of the control arm 400 and is configured for engagement in the stop recess in the bearing 300. Alternate stop designs/configurations are contemplated according to the present disclosure, provided such stop design/configuration may be removably mounted relative to the control arm and functions to limit anterior movement of the bearing.

The tibial component includes a projection 501 configured for mounting in a recess prepared in the proximal end of the resected tibia. The tibial component 500 further includes a platform 502 with a substantially planar superior bearing surface 503 for bearing engagement with the inferior surface 305 of the bearing. A conical recess 504 extends through the platform 502 and into the projection 501. The conical recess is configured for rotational and/or pivotal relative motion receiving the cone 402 of the control arm assembly 400, e.g., through rotational and/or pivotal relative motion.

Figure 11:
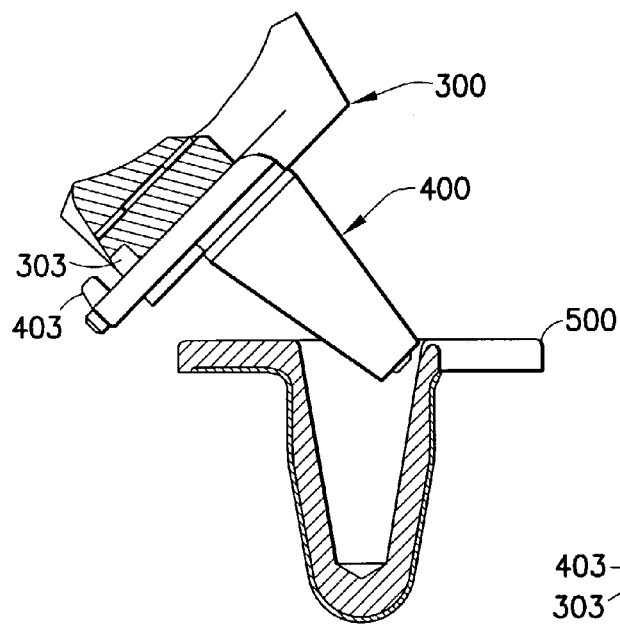
FIG. 11 is a cross-sectional view of the bearing and the control arm being assembled with the tibial component.

The bearing 300 is assembled on to the control arm 400 by sliding the dovetail groove 304 onto the dovetail 401. The assembly is then inserted into the tibial component 500 in the usual fashion as shown in FIG. 11.

In flexion the femoral component 200 will roll backward on the tibial component 500. The bearing 300 moves backward with the femoral component and thus will slide on the dovetailed connection backward on the control arm 400 as shown in FIG. 1.

Figure 12:
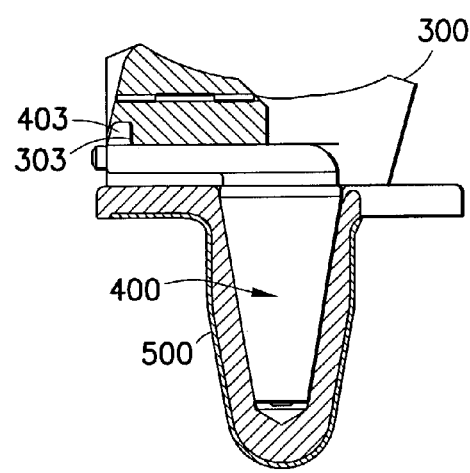
FIG. 12 is a cross-sectional view of the bearing and control arm fully assembled into the tibial component.
Figure 13:
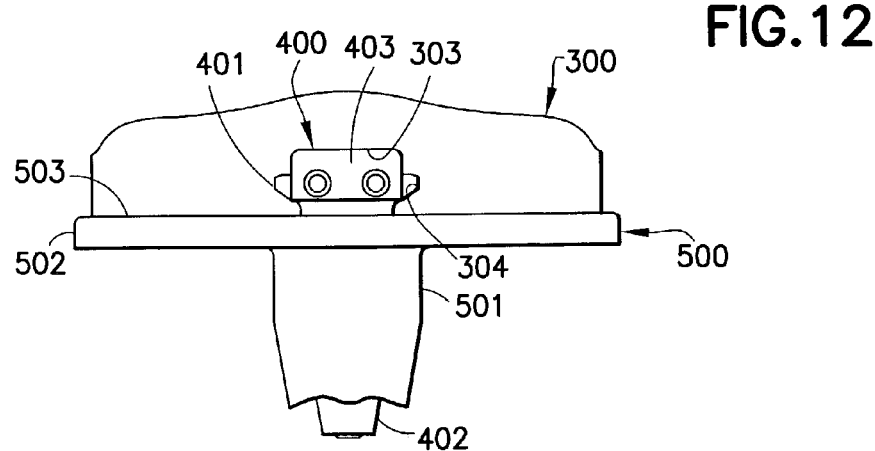
FIG. 13 is a front elevational view of the assembled components of FIG. 12.

During extension the femoral component 200 will roll forward on the tibial component 500. Thus the bearing 300 will also move forward to the position shown in FIG. 12. The stop 403 prevents additional forward motion beyond this point. Such additional motion may result from a lax posterior cruciate ligament, or other reason. This reduces possible impingement with anterior knee tissues thereby reducing anterior knee pain. It also reduces anterior-posterior laxity of the knee.

Revision surgery occasionally is necessary. As noted above, such revision surgery with prior art prostheses could require removal of a properly implanted femoral component merely to disassemble the prosthetic joint and to replace, for example, a defective bearing. With the subject invention, however, it is unnecessary to remove a properly implanted femoral component. Rather, the femoral component can remain in place and disassembly during revision surgery can be achieved easily merely by removing the stop 403. Such removal can be achieved by unthreading the screws 407 which are accessible from anterior portions of the prosthetic component. Implantation of a new bearing can be achieved easily with the femoral component in place by retracting the joint sufficiently to allow the posterior lip of the bearing to clear the condyles of the femoral component.

While exemplary prostheses have been described with respect to various specific embodiments, those of ordinary skill in the art will readily appreciate that various modifications, changes and enhancements may be made thereto without departing from the spirit and scope of the present disclosure.

What is claimed is:

1. A knee joint prosthesis comprising:
a tibial component having a superior bearing surface;
a bearing having an inferior surface in sliding bearing engagement with the superior bearing surface of the tibial component, a groove extending substantially from an anterior extreme to a posterior extreme in the inferior surface of the bearing, a recess formed in the inferior surface of the bearing substantially at an end of the groove adjacent the anterior extreme of the bearing;
a control arm engaged with the tibial component and slidably engaged in the groove of the bearing; and
a stop removably mounted to the control arm and engageable in the recess of the bearing for limiting anterior movement of the bearing on the superior bearing surface of the tibial component; and attachment means for removably attaching the stop to the control arm, the attachment means being accessible at a location adjacent the anterior extreme of the bearing.

2. The prosthesis of claim 1, wherein the control arm includes opposite anterior and posterior ends, the anterior end of the control arm including a notch, said stop being engaged in said notch at the anterior end of the control arm.

3. The prosthesis of claim 1, wherein the attachment means include at least one screw passing through the stop and threadedly engaged in the control arm.

4. The prosthesis of claim 1, wherein the tibial component includes a recess extending into the superior bearing surface thereof, a cone being pivotally mounted in the recess and the control arm being securely mounted to the cone.

5. The prosthesis of claim 1, wherein the bearing further includes a superior articular bearing surface, the prosthesis further comprising a femoral component having an inferior articular bearing surface for articular bearing engagement with the superior articular bearing surface of the bearing.

6. The prosthesis of claim 1, wherein the groove is a dovetail groove and wherein the control arm is a dovetail control arm slidably engaged in said dovetail groove.

7. A prosthetic device comprising:
a first component having a first bearing surface;
a second component having a second bearing surface disposed in sliding bearing engagement with the first bearing surface, the second bearing surface including a groove and a recess formed at one end of said groove; and
a control arm assembly having a pivotal support pivotally engaged with said first component, a control arm securely engaged with said pivotal support for movement with said pivotal support relative to said first component and slidably engaged in said groove and a stop removably mounted to one end of said control arm and configured for releasable engagement in said recess, the stop moving with said control arm relative to said first component as said pivotal support of said control arm assembly pivots relative to said first component, the releasably engagement of said stop with said recess limiting movement of said second component relative to said first component; and wherein the control arm assembly further includes attachment means for removably attaching said stop to said control arm, said attachment means being accessible from one end of said control arm.

8. The prosthesis of claim 7, wherein the attachment means comprises at least one screw passing through said stop and threadedly engaging said control arm.

9. A knee joint prosthesis comprising:
a tibial component having an inferior surface for affixation to a tibia and a superior bearing surface;
a femoral component having a superior surface configured for secure affixation to a femur and an inferior articular bearing surface;
a bearing having an inferior bearing surface for sliding bearing engagement with said superior bearing surface of said tibial component and a superior bearing surface for articular bearing engagement with said inferior articular bearing surface of said femoral component, said bearing having opposite anterior and posterior ends and a dovetail-shaped groove extending along said inferior bearing surface from said anterior end to said posterior end, a recess being formed in said dovetail-shaped groove adjacent said anterior end of said bearing; and
a control arm assembly pivotally mounted to said tibial component and having a dovetail-shaped control arm with opposite anterior and posterior ends, said control arm being slidably engaged in said groove of said bearing, a stop removably mounted to said anterior end of said control arm and configured for releasable engagement in said recess of said bearing, such that said stop limits anterior sliding movement of said bearing relative to said control arm assembly and said tibial component; and wherein the control arm assembly further comprises attachment means for removably attaching said stop to said anterior end of said control arm, said attachment means being accessible at the anterior end of the control arm.

10. The knee joint prosthesis of claim 9, wherein the attachment means comprises at least one screw passing through said stop and threadedly engaged with said control arm.

11. The knee joint prosthesis of claim 9, wherein the bearing is formed from a non-metallic material and wherein said control arm and said stop are formed from a metallic material.

* * * * *